United States Patent [19]
Rabbe et al.

[11] Patent Number: 5,776,198
[45] Date of Patent: Jul. 7, 1998

[54] ADJUSTABLE VERTEBRAL BODY REPLACEMENT

[75] Inventors: Louis-Marie Rabbe, Mantoche, France; Lawrence M. Boyd, Memphis, Tenn.; Jean-Louis Chevalier, Merlimont-Plage; Jean-Charles Moreau, Paris-Plage, both of France

[73] Assignee: SDGI Holdings, Inc., Wilmington, Del.

[21] Appl. No.: 814,115

[22] Filed: Mar. 10, 1997

Related U.S. Application Data

[63] Continuation of Ser. No. 647,272, May 13, 1996, Pat. No. 5,702,453, which is a continuation of Ser. No. 353,566, Dec. 9, 1994, abandoned.

[51] Int. Cl.$^6$ .................................................. A61F 2/44
[52] U.S. Cl. .................................................. 623/17; 606/61
[58] Field of Search .................... 623/17, 22; 606/61, 606/71

[56] References Cited

U.S. PATENT DOCUMENTS

| | | |
|---|---|---|
| 4,553,273 | 11/1985 | Wu . |
| 4,554,914 | 11/1985 | Kapp et al. . |
| 4,599,086 | 7/1986 | Doty . |
| 4,636,217 | 1/1987 | Ogilvie et al. . |
| 4,657,550 | 4/1987 | Daher . |
| 4,820,305 | 4/1989 | Harms et al. . |
| 4,911,718 | 3/1990 | Lee et al. . |
| 4,932,975 | 6/1990 | Main et al. . |
| 5,019,108 | 5/1991 | Bertin et al. . |
| 5,062,850 | 11/1991 | MacMillan et al. . |
| 5,108,395 | 4/1992 | Laurain . |
| 5,147,404 | 9/1992 | Downey . |
| 5,192,327 | 3/1993 | Brantigan . |
| 5,236,460 | 8/1993 | Barber . |
| 5,571,190 | 11/1996 | Ulrich et al. . |
| 5,571,192 | 11/1996 | Schönhöffer . |

FOREIGN PATENT DOCUMENTS

| | | |
|---|---|---|
| 0 179 695 A1 | 4/1986 | European Pat. Off. . |
| 0 567 424 A1 | 10/1993 | European Pat. Off. . |
| 41 09 941 A1 | 1/1992 | Germany . |

OTHER PUBLICATIONS

*Titanium—Mesh-Cylinder*, Miami Moss, 1989.

*Primary Examiner*—Michael J. Milano
*Attorney, Agent, or Firm*—Woodard, Emhardt, Naughton Moriarty & McNett

[57] ABSTRACT

An adjustable vertebral body replacement implant and assembly includes a thin-walled cylindrical body configured to span over most of the length between intact vertebrae when damaged or diseased vertebrae have been removed. The cylindrical body defines a hollow interior with a plurality of bone-ingrowth apertures communicating with the interior. The replacement assembly further includes endplates configured to contact the adjacent vertebra and to engage the cylindrical body therebetween. The cylindrical body and the endplates include mating threads to permit adjustment of the overall height of the implant. A means for fixing the cylindrical body to the endplates is contemplated, which in one embodiment is a set screw for locking the components in place. In another embodiment, the means for fixing includes a crimping channel and notch defined in the endplates to be crimped onto the cylindrical body. A means for connecting the replacement implant to a longitudinal member is provided, which in one embodiment contemplates a clamp and screw assembly. In another embodiment, the means for connecting includes an arm projecting from the endplates with an opening to receive the longitudinal member therethrough.

23 Claims, 6 Drawing Sheets

ADJUSTABLE VERTEBRAL BODY REPLACEMENT

This application is a continuation of application Ser. No. 08/647,272, filed May 13, 1996, now U.S. Pat. No. 5,702, 453, which is a file wrapper continuation of application Ser. No. 08/353,566, filed on Dec. 9, 1994 and now abandoned.

BACKGROUND OF THE INVENTION

The present invention concerns an implant for replacement of one or more vertebral bodies and their adjacent disks. More particularly, the vertebral body replacement is particularly well suited for implantation through an anterior approach.

The treatment of injuries to the spine has advanced significantly since the days of the first recorded surgical procedure for spinal cord injury in the late 7th Century. The techniques, instrumentation and implants have changed over the years and have been better adapted to address many forms of spinal injury and deformities that can occur due to trauma, disease or congenital effects. One type of spinal deformity, a kyphosis, involves a prolapse of the vertebral column towards the front of the body, often caused by the destruction of the vertebral body itself. This destruction can be in the form of a trauma type injury, such as a fracture or burst injury to the vertebral body, or a non-traumatic deformity caused by a tumor or a degeneration of the bone in the vertebral body.

Treatment of a kyphosis in the thoracic or lumbar spine appears now to be best achieved through an anterior approach, particularly in order to avoid some of the more severe complications associated with support or replacement of a damaged vertebral body. In most treatments of a kyphosis, a high degree of anterior reconstruction of the spine is required, most frequently involving total removal of the damaged vertebral body. In a typical anterior approach, partial or total ablation of the vertebral body and the two adjacent vertebral disks is carried out. The remaining space is then distracted to manipulate the spine to its correct orientation.

In many cases, the space is filled with a polymerizable paste or a bone graft which is frequently modeled to give it the shape of the destroyed vertebral body. Frequently, autologous bone, such as that extracted from the ilium, is used to bridge the space. The polymerizable paste can include a PMMA bone cement. Once the cavity remaining after the removal of the original vertebral body has been filled, an osteosynthesis instrument is positioned between the adjacent unaffected vertebrae to prevent any relative movement therebetween. The osteosynthesis device is essential to restabilize the vertebral column, to support the loads to which the thoracic or lumbar spine is exposed, and to enhance the likelihood and quickness of union of the bone graft material with the adjacent vertebral bodies. Once the bone graft and material is sufficiently solid, the osteosynthesis device normally is not subjected to any further mechanical stresses.

A known osteosynthesis device is depicted in U.S. Pat. No. 5,108,395 to Jean-Marie Laurain, the disclosure of which is incorporated herein by reference. This system is illustrated in FIGS. 1 and 2 of the present application. Referring first to FIG. 1, it can be seen that a damaged vertebra $V_3$ includes a destroyed vertebral body $C_3$. An interior implant 1 is provided for bridging between the two intact vertebrae $V_2$ and $V_4$ to permit removal of the damaged vertebra $V_3$ and its adjacent disks $D_2$ and $D_3$. The anterior implant 1 includes a pair of clamps 2 which are engaged to the intact vertebral bodies by way of a number of spikes 3. In addition, the clamps 2 are maintained in position by bone screws 5 extending through screw holes 11, lateral lugs 8 of the clamps. The implant 1 also includes a plate 6 which is configured to span between the intact vertebrae and is strong enough to support the loads generated in the spinal column at that location.

Each clamp 2 includes a threaded post 12 projecting therefrom which is configured to pass through a corresponding opening 14 at each end of the plate 6. A nut 7 is adapted to engage the threaded post 12 to fix the plate 6 to each of the clamps 2. The surface of the clamps 2 include serrations 15 which mate with corresponding serrations 16 at each end of the plate 6, thereby permitting differing angular orientations of the plate relative to each of the clamps. An opening 9 is provided through the threaded post 12 of the clamps to receive another bone screw 5 for firm fixation of the clamp with the healthy vertebral bodies $V_2$ and $V_4$.

An important feature of the system described in the '395 patent is the provision of notches 18 in each of the clamps 2. The notches are configured to receive the tips of a forceps 19 which is used to provide a distraction force between the two vertebrae $V_2$ and $V_4$. As shown in FIG. 2, once the clamps 2 are fixed to the corresponding intact vertebrae, the forceps 19 are used to distract and permit room for placement of a bone graft G. Once the bone graft is in place, the anterior plate 6 can be attached to each of the clamps 2 in the manner previously described. Once the plate is in position, the distraction forceps 19 is removed and the nut 7 tightened to form a rigid construct.

The anterior construct shown in the '395 patent and in FIGS. 1 and 2 of this application is one system for providing anterior fixation with the use of autologous or allogenic bone graft material. Other implants have been devised which rely upon an additional element interposed between the adjacent vertebra, in lieu of or in addition to the traditional bone graft material. One such device is shown in the patent to Harms et al. U.S. Pat. No. 4,820,305, which is sold as the "Harms Cage" by the Biedermann-Motech Company. This device contemplates a hollow cylindrical mesh which is inserted in the gap between adjacent vertebra, with bone graft material being disposed inside the hollow interior of the mesh.

The patent to Brantigan, U.S. Pat. No. 5,192,327, shows a device similar to the "Harms Cage" which is composed of a number of hollow oval-shaped implants within which bone graft material is disposed. European Patent No. 0 179 695 to Kehr shows a rigid inert body having a number of passageways extending between the intact vertebrae into which bone growth material can be implanted. In addition, the device shown in the Kehr European patent includes a plate spanning between the vertebrae having holes for receiving bone screws therethrough.

Another variety of implant devices particularly suited for replacement of vertebral bodies include components of generally solid construction which completely occupy the empty vertebral space. These devices are represented by the patents to Kapp et al., U.S. Pat. No. 4,554,914; Doty, U.S. Pat. No. 4,599,086; Ogilvie et al., U.S. Pat. No. 4,636,217; and Downey, U.S. Pat. No. 5,147,404. Each of these devices is provided with a spike or similar mechanism for engaging the end plates of the intact vertebrae to maintain the implant in position. A similar construction is followed in the U.S. Pat. No. 5,062,850 to MacMillan et al., although this device includes open space between support columns of the axially fixed vertebral body prosthesis.

In each of the former patents, the implant device requires separate distraction of the intact vertebrae prior to insertion of the device. The following patents show vertebral prosthesis which include some feature for expansion of the device in situ. For example, the Main et al., U.S. Pat. No. 4,932,975, and Barber U.S. Pat. No. 5,236,460 show prostheses that telescope through the admission of a hydraulic fluid. The patents of Rezaian, U.S. Pat. No. 4,401,112; Wu, U.S. Pat. No. 4,553,273 and Daher, U.S. Pat. No. 4,657,550 show devices that expand in situ the manipulation of a threaded component. In addition, the Rezaian patent shows a turnbuckle construct of this type with the addition of a spiked plate engaged in the opposite intact vertebrae to strengthen the construct.

In recent years, the application of anterior approaches to instrumenting the spine has become more prevalent. As these anterior approaches advance, it becomes of greater necessity to provide a vertebral body replacement that meets all of the benefits of anterior surgery without the detriments of the several prior devices. Each of the above-mentioned vertebral body replacements suffer from one or more disadvantages. For instance, some of the devices do not provide means for osteosynthesis between the intact vertebrae. These devices lack, features that can either permit bone ingrowth or facilitate placement of bone graft between adjacent healthy vertebrae. It is recognized that a more permanent and stable correction of a kyphotic condition occurs with fusion of a bony mass in place of the replaced vertebra. Thus, any vertebral body replacement should accommodate this aspect. Other vertebral prosthesis offer no means for adjusting the size of the implant to accommodate the specific vertebral anatomy. Further, other of the devices do not contemplate some auxiliary fixation to help provide a stable construct. Each of these needs, and many others, are met by the vertebral body replacement according to the present invention.

SUMMARY OF INVENTION

The present invention contemplates a vertebral replacement implant and assembly for fixation of the implant in the space left by a removed vertebra between two intact vertebrae. In one aspect, the implant includes a thin-walled cylindrical body sized to occupy a substantial portion of the space between the intact vertebrae. The cylindrical body is hollow with a plurality of apertures through the wall of the body in communication with the interior, to permit bone ingrowth once the implant is implanted. The opposite ends of the cylindrical body carries continuous threads, preferably on the outer surface of the body.

The inventive implant further contemplates a pair of endplates having a surface directed against a corresponding one of the intact vertebrae when the prosthesis is implanted. The endplates each include a cylindrical portion extending from the end surface, which portion includes threads for mating with the threaded ends of the cylindrical body. Preferably, the threads of the endplates are internal to the cylindrical portion. In one aspect, the endplates are themselves hollow to provide communication between the hollow interior of the cylindrical body and the adjacent intact vertebrae. Alternatively, the invention contemplates the addition of an end cap to the implant to close the end surface of the endplates against the adjacent vertebrae in order to provide additional support for weak vertebrae.

Another feature of the invention resides in the provision of means for fixing the cylindrical body to each of the endplates to prevent unthreading of the mating threads of the three components of the implant. In one embodiment, the means for fixing includes apertures in the threaded portion of the endplates which are threaded to accept a set screw. Preferably, two set screws are threaded into two such apertures in the endplates to apply a clamping pressure against the cylindrical body engaged with the endplate.

In another embodiment, the means for fixing contemplates a crimpable cylindrical portion of the endplates. In one aspect, the cylindrical portion includes an annular ring, dissected by a crimping notch. The application of a crimping force around the annular ring reduces the notch, and thereby reduces the circumference of the cylindrical portion so it is tightly engaged about the cylindrical body threaded therein.

Another inventive aspect resides in the provision of means for connecting the implant to a longitudinal member extending outside the space left by the removed vertebrae. The longitudinal member may be a plate or a rod that is fixed in a known manner to the adjacent intact vertebrae. Preferably, the longitudinal member can be used to assist in the distraction of the intact vertebrae for insertion of the vertebral replacement implant.

In one embodiment, the means for connecting includes a clamp configured to clamp onto the longitudinal member. The clamp supports a screw directed towards the replacement implant when it is interposed between the intact vertebrae. The cylindrical body of the implant includes a number of apertures threaded to receive the connecting screw. The clamp is preferably slidable along the length of the longitudinal implant to facilitate alignment of the screw with the number of threaded apertures of the cylindrical body. In addition, the clamp includes a spherical seat, and the screw includes a spherical head to permit varying angular orientations of the screw relative to the longitudinal member.

In another embodiment, the means for connecting includes an arm extending from a flange of the endplates. The free end of the arm defines an opening through which the longitudinal member extends. A set screw intersects the opening to provide fixation of the longitudinal member to the arm of the endplates.

One object of the present invention is to provide a vertebral body replacement implant configured to support the space left by removal of a damaged or diseased vertebra. One objective is to provide an implant that can be easily adjusted to vary the overall length of the implant dependent upon the vertebral level into which the implant is interposed. A further objective of the inventive implant is to permit this length adjustment yet provide means for fixing the components to prevent disengagement or unthreading.

A further object is achieved by the present invention by the provision of means for connecting the vertebral replacement implant to a longitudinal member extending along the length of the spine between the adjacent intact vertebrae. The longitudinal member can be used for distracting the space left by the removed vertebra to facilitate insertion of the replacement implant. Yet another object is to provide an implant that can house bone growth material to facilitate fusion of the instrumented level.

One benefit of the vertebral body replacement of the present invention is that it provides a strong implant to support the spinal loads while awaiting fusion of bone growth material between the intact vertebrae. A further benefit is that the implant can be more easily adjusted to accommodate spaces at different vertebral levels.

Other objects and benefits of the invention can be gleaned from the following written description of the invention, considered together with the accompanying figures and claims.

DESCRIPTION OF THE PREFERRED EMBODIMENTS

Figure 1:
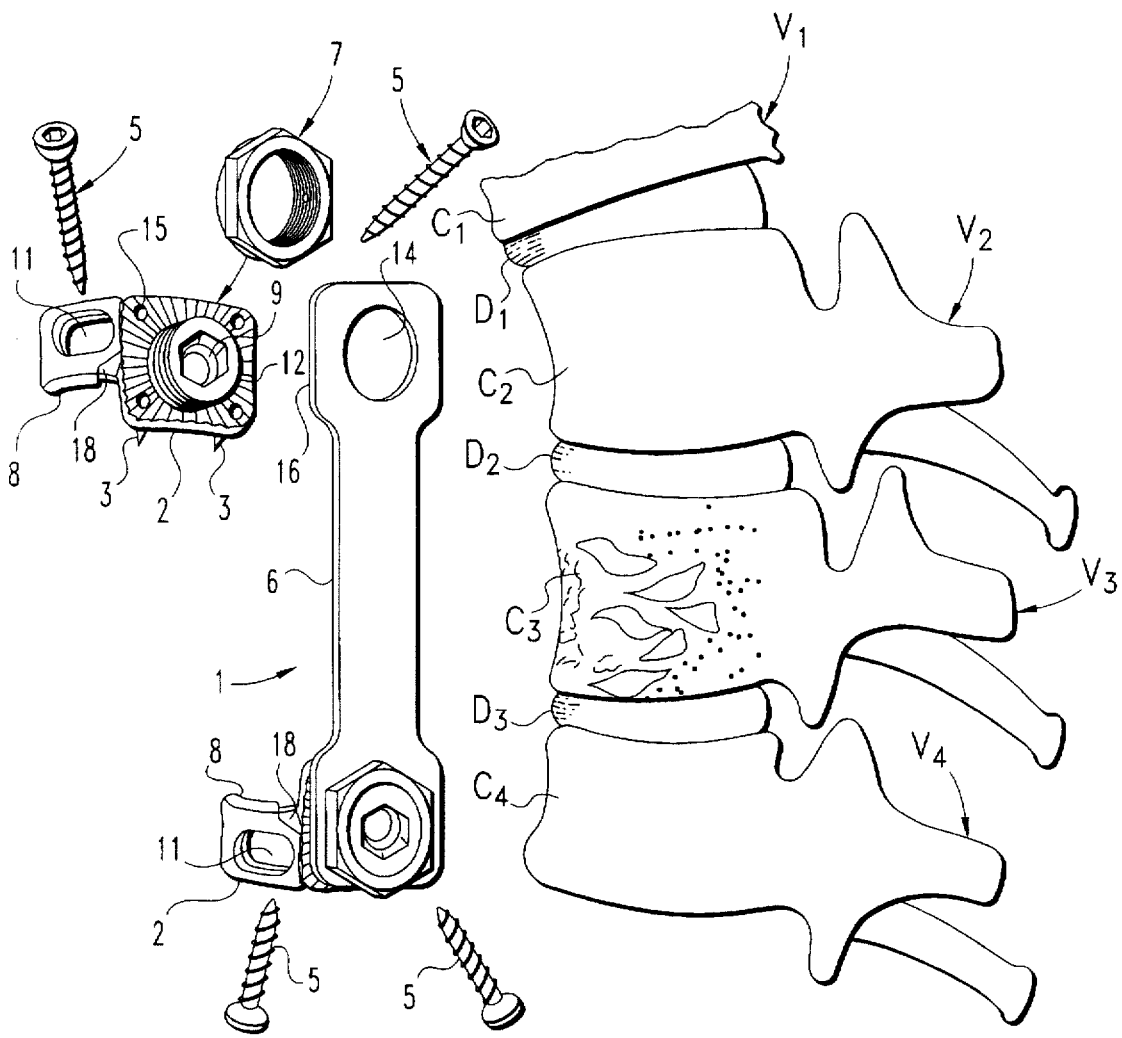
FIG. 1 is an exploded perspective view of a spinal osteosynthesis implant according to the prior art U.S. Pat. No. 5,108,395.

For the purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Figure 3:
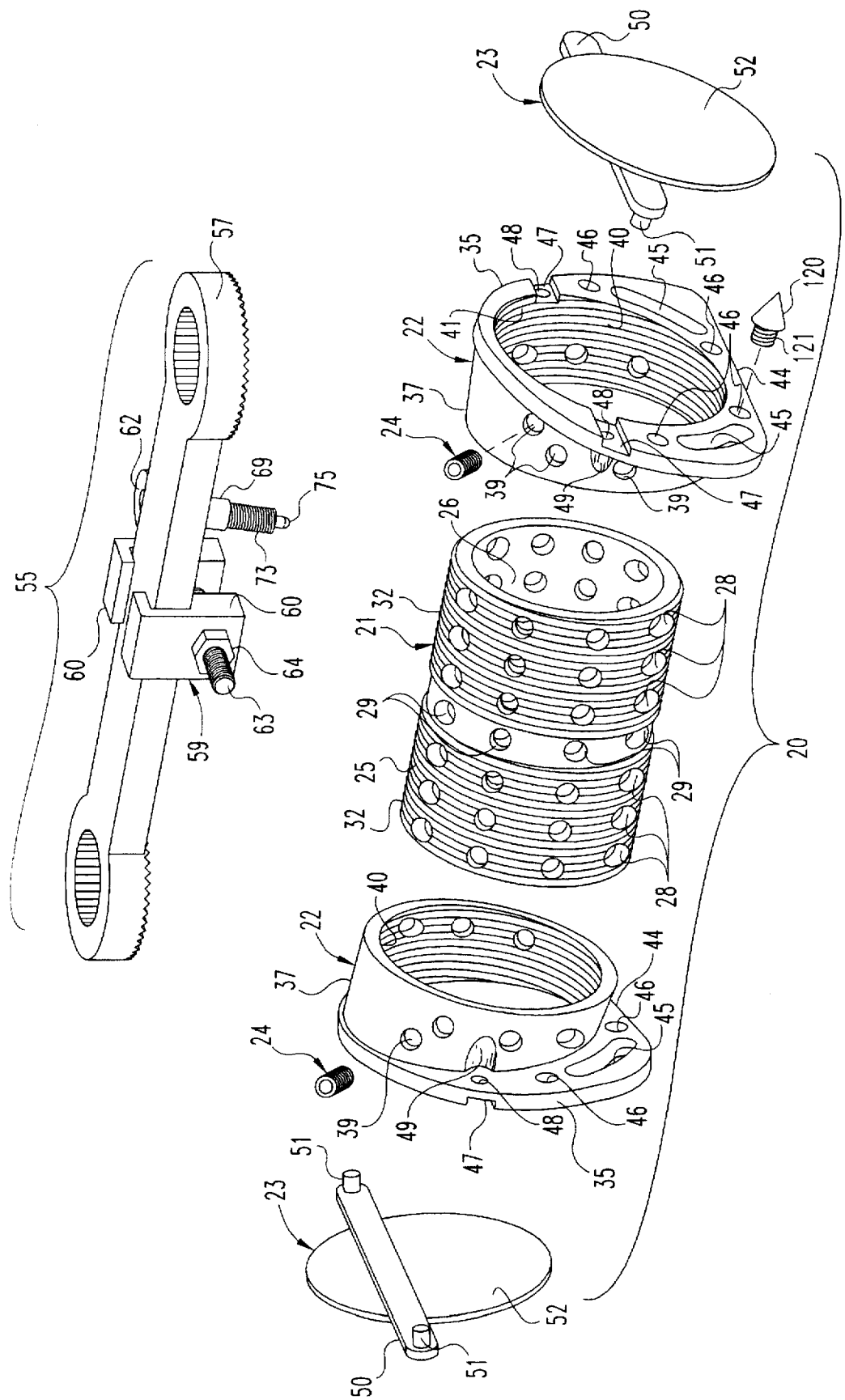
FIG. 3 is an exploded perspective view of a vertebral body replacement assembly in accordance with one embodiment of the present invention.

Referring now to FIG. 3, a vertebral body replacement assembly 20 is shown in accordance with one embodiment of the present invention. The assembly 20 generally includes a threaded cylindrical body 21, threaded endplates 22 and end caps 23. A set screw 24 is also provided as one embodiment of a means for fixing each of the endplates 22 to a corresponding end of the cylindrical body 21. In one specific embodiment, the set screw 24 is a breakable locking screw in which the head of the screw shears off when the tightening torque limit is reached. Such a locking screw is disclosed in co-pending French patent application No. 94 10 377, filed on Aug. 29, 1994.

The threaded cylindrical body 21 is formed from a cylindrical wall 25 which defines a hollow cavity 26 therein. The cavity is configured to receive bone osteosynthesis material, which may be in the form of autogenous or allograph material. The cylindrical wall 25 is provided with a plurality of apertures 28 in communication with the cavity 26. These apertures provide a path for bone or tissue ingrowth to further enhance the stability of the implant. The cylindrical wall 25 includes a second plurality of threaded apertures 29 generally in the middle of the implant, which are configured to engage the support assembly 55 as described in more detail herein.

In one important feature of the cylindrical body 21, the opposite ends of the cylindrical wall 25 are formed into external threads 32. In one specific embodiment, the threads 32 extend from each opposite end over most of the total length of the threaded cylindrical body 21 and are configured to engage the threaded endplates 22. Each endplate includes a flange 35, which preferably assumes a shape to cover a substantial load-bearing area of the end plates of the adjacent intact vertebral bodies. A cylinder 37 is integrally formed with flange 35 to extend toward the threaded cylindrical body 21 when the endplates 22 are placed within the excised vertebral space. The cylinder 37 of each endplate includes a number of threaded openings 39 adapted to receive a set screw 24 therein.

The cylinder 37 and flange 35 of the endplates 22 define a bore 40 therethrough. The inside surface of the bore 40 is provided with internal threads 41 which are configured to mate with the external threads 32 of the cylindrical body 21. In the preferred embodiment, the threads 41 extend along at least the entire length of the cylinder 37 and preferably into the flange 35.

Figure 4:
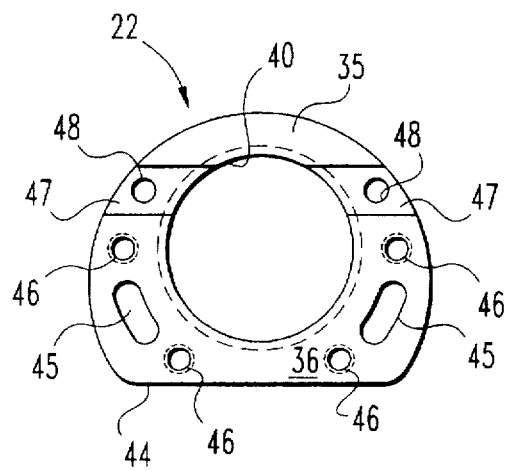
FIG. 4 is an end elevational view of an endplate used in connection with the vertebral body replacement assembly shown in FIG. 3.
Figure 5:
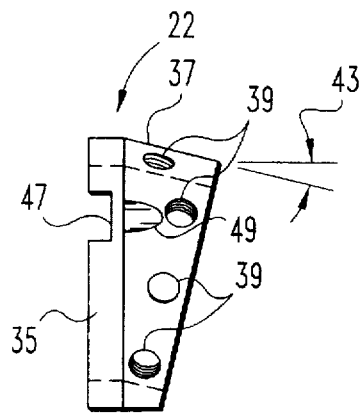
FIG. 5 is a side elevational view of an endplate used with the vertebral body replacement assembly of FIG. 3.

Further details of the endplates 22 can be seen in FIGS. 4 and 5. As shown in FIG. 5, the cylinder 37 is integrally formed with the flange 35 to define a lordosis angle 43. This angle is intended to permit use of the vertebral body replacement assembly 20 to replace a damaged vertebra, such as vertebra $V_3$ shown in FIG. 1, and still maintain the normal lordotic curvature of the spine at that level. The end face 36 of the flange 35 is provided with vascularization apertures 45 extending through the flange. These apertures 45 are intended to provide an avenue for vascularization of the space between the adjacent vertebrae. The end face 36 can be provided with four spikes, such as spikes 91 shown in the embodiment of FIG. 7. Alternatively, spikes 120 (FIG. 3) can be provided that include a threaded stem 121 to be engaged in threaded apertures 46 defined in end face 36. In either case, the spikes (91, 120) are configured to penetrate the end plate of the adjacent vertebra to help maintain the position of the implant in situ.

The end face is further provided with a mounting slot 47 passing across the flange 35 and spanning along a chord of the internal bore 40. Within each mounting slot is an aperture 48 passing therethrough. The cylinder 37 of the endplate 22 is provided with a mounting notch 49 that is aligned with each aperture 48 in the mounting slot 47. This slot 47, aperture 48 and notch 49 are configured to support an end cap 23, as herein described. Referring back to FIG. 3, the end cap 23 includes a generally rectangular support bar 50 which is mounted to span across a chord of the flat circular plate 52 of the end cap. At each end of the support bar 50 is an outwardly projecting lug 51. Each lug 51 is sized to be received within a corresponding aperture 48, while the support bar 50 is itself configured to fit within the mounting slot 47 in the flange 35. Further, each lug 51 slides conveniently into a corresponding mounting notch 49 in the cylinder 37. In this manner, the end cap 23 is held in position, particularly when the replacement body assembly is disposed between the adjacent intact vertebrae $V_2$ and $V_4$.

The end cap 23 provides additional support for the implant between the adjacent intact vertebrae. The end cap can be eliminated if bone growth between the adjacent vertebrae and through the replacement body is preferred. Alternatively, the plate 52 of each end cap 23 can be perforated to permit bone ingrowth between the vertebral end plates and the bone growth material disposed within the threaded cylindrical body 21. In the preferred embodiment, the endplates are shown solid to provide the maximum load bearing capability for loads along the length of the vertebral column.

In the illustrated embodiment, the threads 32 on the cylindrical replacement body are external threads, while the threads 40 in the endplates are internal. Alternatively, the cylinder 37 of the endplates can carry external threads and the cylindrical replacement body carry internal threads in the cavity 26. In this latter instance, the inner diameter of the cylindrical body would naturally be slightly greater than the outer diameter of the cylinder of the endplates.

In the preferred embodiment, the cylindrical wall forming the implant 21 can be relatively thin, when compared against replacement bodies of the prior art. In one specific embodiment, the wall is one (1) mm. thick. Since the primary load endured by the implant will be axial compression, rather than bending, a thin-walled cylinder is appropriate and even desirable.

It is also preferred that the implant 21 include a large number of apertures 28, 29 to promote tissue ingrowth and vascularization, thereby enhancing the stability of the construct after fusion has occurred. In one specific embodiment, the total area of the plurality of apertures is at least twenty five percent (25%) of the surface area of the cylindrical body 21.

Figure 2:
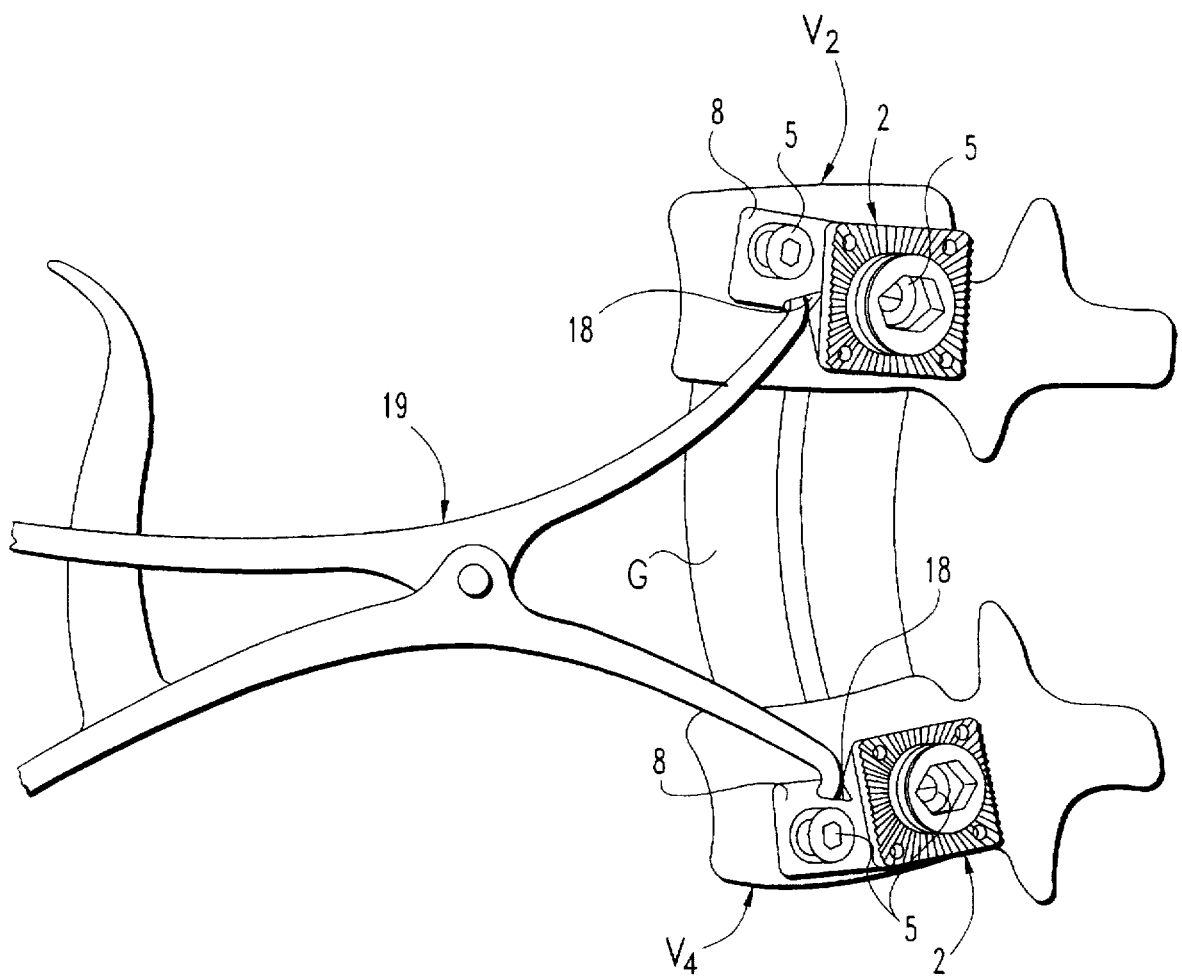
FIG. 2 is a view showing a portion of the view of FIG. 1 with the addition of an instrument for permitting positioning of a graft between the vertebrae carrying the clamps associated with the prior device of the '395 patent.

In use, the damaged vertebra, such as vertebra $V_3$ shown in FIG. 1, is removed. In one embodiment, the clamps 2 of the interior implant 1 shown in FIGS. 1 and 2 are engaged to the intact vertebral bodies in the manner shown in FIG. 2. Also shown in FIG. 2, the forceps 19 can be used to distract the intact vertebrae to permit implantation of a vertebral body replacement assembly 20. In the preferred method, the optimum vertebral height is determined and the threaded cylindrical body 21 and threaded endplates 22 are fitted together to achieve that proper height. Specifically, each of the end caps can be threaded onto the threaded cylindrical body 21 until the desired height is attained.

It is important that the bottom edge 44 of the flange 35 of each of the endplates be generally oriented in the same way between the two threaded endplates 22. This orientation is important because the replacement assembly 20 will be disposed between the two intact vertebrae, bearing against the end plates of those vertebrae. In order to maintain the maximum load bearing capability, the flanges 35, and particularly the end face 36, assume the shape of the vertebral body against which the endplates bear and are sized to occupy as much area of the intact vertebral body end plate as possible.

Figure 11:
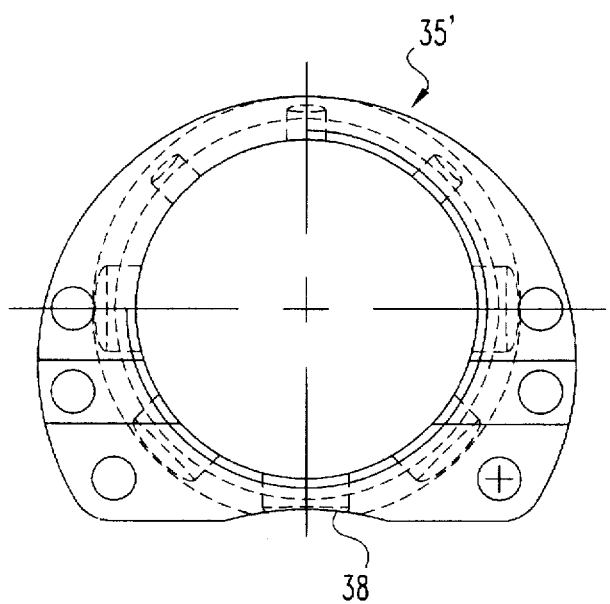
FIG. 11 is an end elevational view of one specific endplate used in connection with the vertebral body replacement assembly shown in FIG. 3 in the thoracic spine.

Preferably, three such shapes are provided to accommodate the anatomic variations of the vertebral bodies at the lumbar, thoraco-lumbar and thoracic levels, the configuration of the flange 35 shown in FIG. 4 is applicable to the thoraco-lumbar vertebrae. A smaller, more rounded, configuration can be provided for implantation at the thoracic level, such as the flange 35' shown in FIG. 11. The flange 35' is also shown as including a relief radius 38 to increase the clearance between the flange and the dural space housing the spinal cord. This relief radius 38 is preferably included in all three shapes of the endplate flanges.

In one specific embodiment, the external threads 32 on the threaded cylindrical body 21 are cut in opposite directions so that the endplates can be drawn together or apart by rotating only the cylinder. Thus, as the cylinder is rotated in one direction, the threads 32 at each of the ends engage the internal threads 41 of each of the end caps 23 in the right direction to draw the end caps together. Alternatively, the handedness of the threads 32 can be the same at each end so that it is necessary to individually thread each end cap in opposite directions onto the cylindrical body 21. The disadvantage of this arrangement is that it is more difficult to adjust the height of the total assembly 20 while maintaining the proper orientation of each of the lower edges 44 of the end face 36. An advantage is that in situ the assembly is unable to unthread itself.

Once the endplates and threaded cylindrical body have been engaged in the proper orientation for the correct height, the set screws 24 are threaded into an appropriate one of the threaded openings 39 in the cylinder 37 of the endplates 22, in order that the set screw 24 extend into contact with the threaded cylindrical body 21. The set screws 24 (which can be the breakable locking screws mentioned above) exert a clamping pressure against the body 21 to hold it in place. Thus, the set screws 24 provide a means for fixing the components together and prevent rotation of the cylindrical body 21 with respect to either of the endplates 22. Preferably, two set screws are used at each endplate 23 to firmly fix the associated ends of the threaded cylindrical body 21. To ensure that the set screws 24 achieve firm purchase on the body 21, the apertures 28 in the threaded body have a smaller diameter than the set screws 24.

With the cylinder and endplates thus fixed at their proper height dimension, bone graft material can then be inserted into the bore 40 of the endplates and cavity 26 of the cylindrical body 21. After the interior of these components has been completely filled with bone graft material, the endplates 23 are placed in position with the lugs 51 extending through apertures 48, and with support bar 50 passing through mounting slot 47 in each endplate. The replacement assembly 20 can then be disposed between the distracted vertebrae $V_2$ and $V_4$. Once the assembly is properly positioned with the end faces 36 of each of the endplates 22 properly oriented on the vertebral end plates, the distraction forceps 19 are removed so that the assembly 20 is clamped in place between the two vertebrae.

In order to further ensure that the replacement assembly 20 will not migrate or slip in its position between the intact vertebrae, a support assembly 55 may be provided. In the preferred embodiment, this support assembly 55 is configured to mate with the clamps 2 used with the anterior implant system of the prior art shown in FIGS. 1 and 2. The support assembly 55 can also be used with other anterior plates, such as the Z-PLATE ATL* sold by Danek Medical, Inc., or rod systems such as the CD Hopf System of Sofamor, S.N.C.

In particular, the support assembly includes a stabilization plate 57, which can be configured substantially similar to the plate 6 shown in FIG. 1, including the serrations on the bottom face of the ends of the plate. Means for connecting the vertebral replacement body assembly 20 to the plate 57 includes a clamp assembly 59 is provided which firmly grips the plate 57 to support a locking screw 69. The clamp assembly 59 includes a pair of clamp halves 60 which are preferably in the shape of a C to grip and support the plate 57. Each of the clamp halves 60 include an aperture (not shown) which receives a threaded rod 63 of an adjustment plate 62. A nut 64 is threaded on the rod 63 to draw the clamp halves 60 together about the stabilization plate 57.

Figure 6:
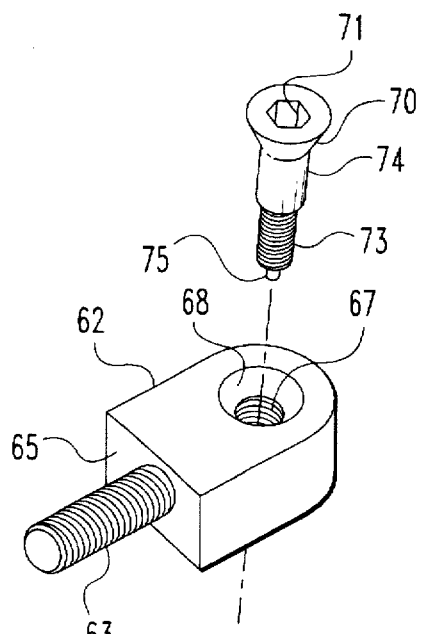
FIG. 6 is a perspective exploded view showing a component of the clamp assembly used with the vertebral body replacement assembly shown in FIG. 3.

The details of the adjustment plate 62 are shown more clearly in FIG. 6. The adjustment plate includes the threaded rod 63 extending from a face 65 of the plate 62. The plate 62 also includes an aperture 67 therethrough having a spherical seat surface 68 into which a corresponding spherical head 70 of the locking screw 69 is received. The locking screw 69 includes a hex recess 71 in its head to accept a driving tool. The locking screw 69 also includes a threaded shank 73 which is adapted to engage one of the threaded apertures 29 in the threaded cylindrical body 21. To help guide the locking screw 69 into position, a guide nub 75 is provided having a smaller diameter than the threaded shank 73. The locking screw 69 preferably includes smooth shank 74 between the head 70 of the screw and the threaded shank 73.

In use, the clamp halves 60 can be tentatively attached but not clamped to the stabilization plate 57. The stabilization plate 57 can then be engaged to the clamps 2 in each of the intact vertebral bodies and fixed in place by a corresponding nut, such as nut 7 shown in FIG. 1. With the stabilization plate 57 thus attached between the distracted vertebrae, the distraction forceps 19 can be removed so that the full load of the spinal column can be borne by the replacement assembly 20. Once the distraction forceps have been removed, the clamp halves 60 can be adjusted along the length of the plate 57 so that the locking screw 69 is aligned with an appropriate one of the threaded apertures 29 in the threaded cylindrical body 21. The spherical contact between the head 70 of the locking screw 69 and the spherical seat 68 of the adjustment plate 62 allows the locking screw to assume whatever angle is necessary to engage a threaded aperture 29. As so aligned, the locking screw 69 can then be easily threaded into one of the apertures 29 until it is locked between the adjustment plate 62 and the threaded cylindrical body 21. At this point then, the clamp halves 60 can be fully clamped onto the plate 57 by tightening the nut 64 on the threaded rod 63.

In another embodiment of the invention, a vertebral body replacement assembly 80 is configured for connection to an elongated distraction or compression rod. In this embodiment, the assembly 80 includes opposite endplates 83 which are configured to threadedly engage a cylindrical body 21. (This cylindrical body 21 is substantially identical in all respects to the cylindrical body 21 described with respect to FIG. 3). With this embodiment, the endplates 83 include a flange 85 and a cylinder 87 projecting therefrom. The cylinder 87 includes a threaded bore 88 which is threaded to accept the external threads 32 of the cylindrical body 21. Like the prior endplates, the endplate 83 includes a plurality of vascularization apertures 89 formed through the flange 85. The end face 86 of the flange 85 includes a number of spikes 91 projecting therefrom. The spikes are configured to penetrate the end plate of the adjacent vertebral bodies to help maintain the position of the implant in situ.

Figure 7:
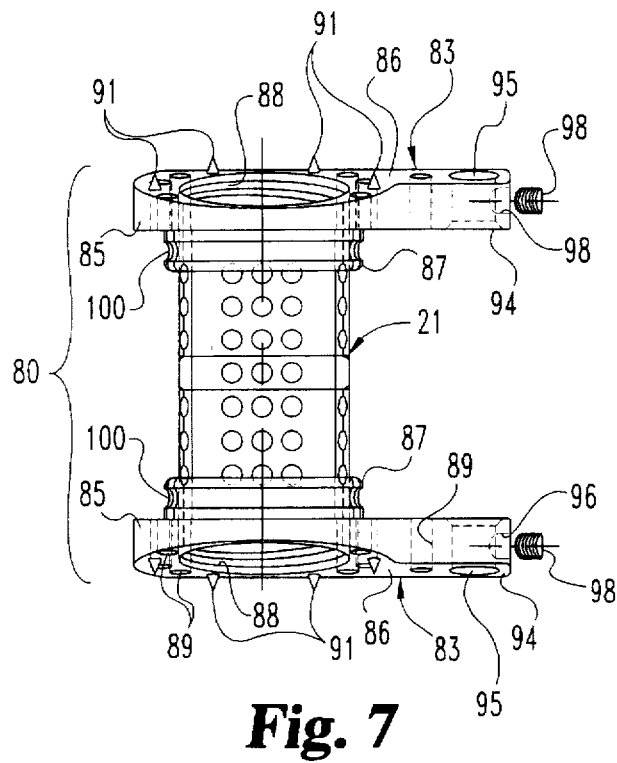
FIG. 7 is a side elevational view of a vertebral body replacement assembly in accordance with another embodiment of the invention, particularly for use with an elongated rod spanning the vertebral sections.
Figure 8:
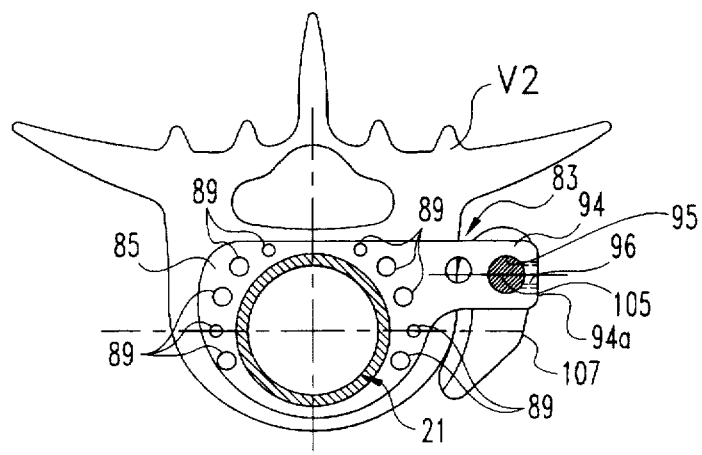
FIG. 8 is an end elevational view of the vertebral body replacement assembly shown in FIG. 7, with the assembly shown in position on a intact vertebra.

As shown in FIGS. 7 and 8, the endplates 83 include an arm 94 projecting from the flange 85, which is a component of a means for connecting the implant to a longitudinal member, such as rod 105. A rod bore 95 is defined adjacent the free end 94a of the arm 94, with a set screw bore 96 intersecting the rod bore 95 from the free end of the arm 94. A set screw 98 is provided which is engaged within the set screw bore 96 to clamp a rod passing therethrough.

Figure 9:
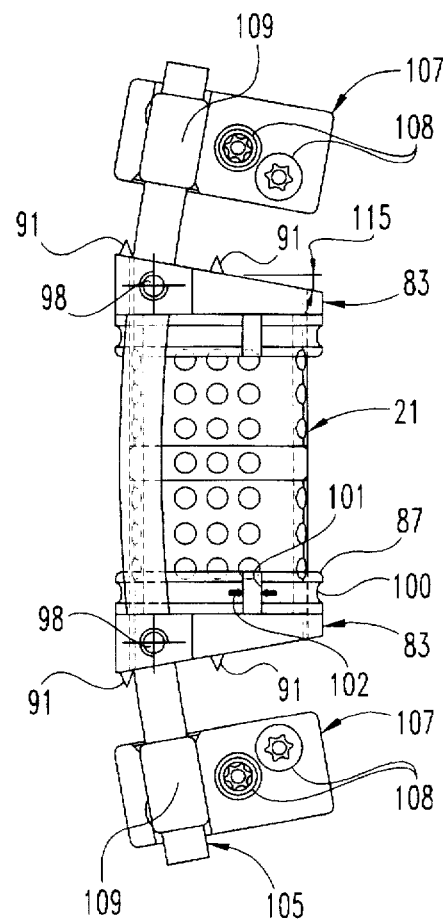
FIG. 9 is a side elevational view of the assembly shown in FIG. 7 as engaged to an elongated rod.

The manner of using the replacement assembly 80 in this embodiment is shown in FIGS. 8 and 9. In particular, the endplates 83 are engaged in the appropriate vertebrae by way of spikes 91. Again, the plates are configured to define an angle 115 to correspond to the proper spinal anatomy at the particular vertebral level. A distraction plate 107 is mounted into each of the intact vertebrae by way of bone screw 108. The plate 107 includes a collar 109 integrally formed thereon through which a distraction rod 105 passes. The distraction rod also extends through each of the rod bores 95 in the arms 94 of the endplates 83. With the rod extending through each of the bores, the set screws 98 fix the endplates in position. Distraction of the adjacent vertebrae can be achieved by an appropriately formed instrument that can engage the collars 109 of each of the distraction plates 107 mounted into the respective vertebrae. A set screw (not shown) can be provided to fix the rod 105 within each collar 109.

Figure 10:
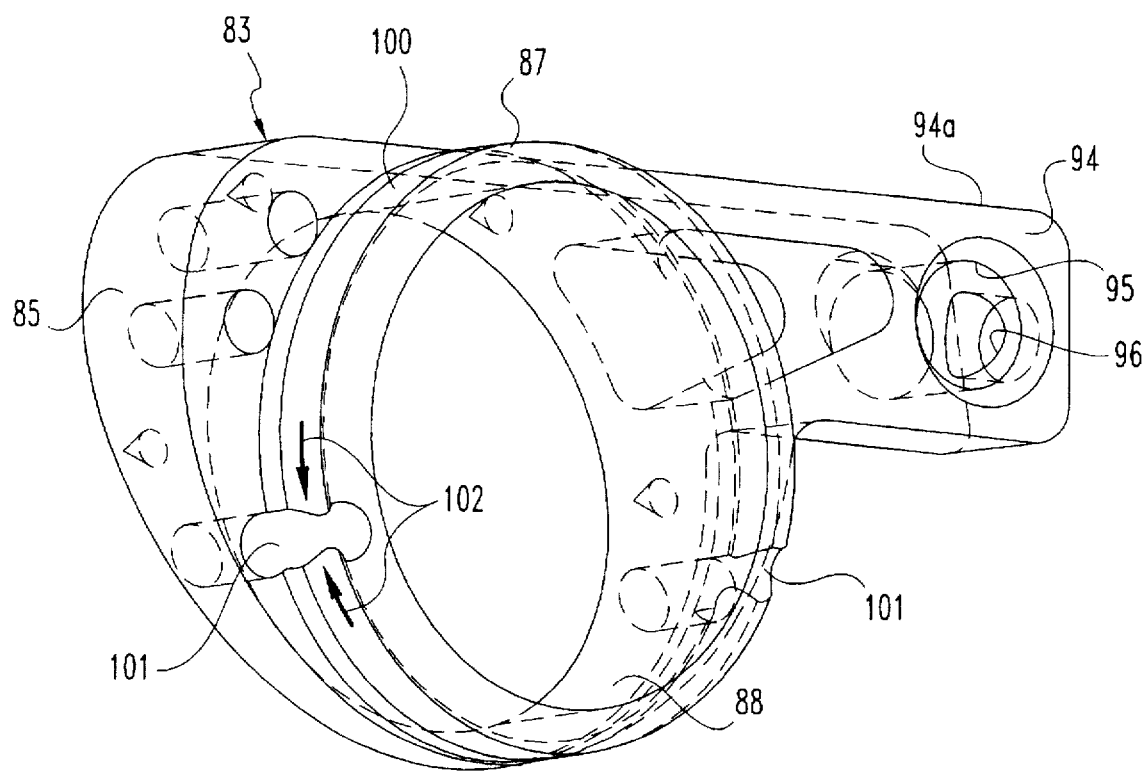
FIG. 10 is a perspective view of the endplate used with the vertebral body replacement assembly shown in FIG. 7.

Referring to FIGS. 7, 9 and 10, details of the manner in which the endplates are fixed to the threaded cylindrical body is described. In particular, the endplates 83, and particularly the cylinder 87 of the endplates, is provided with a a means for fixing in the form of a crimping channel 100 around the diameter of the cylinder. At opposite sides of the cylinder, a crimping notch 101 is provided in the channel 100. In essence, this crimping notch is a gap in the outer circumference of the channel 100. This crimping notch provides a gap which can be closed by an appropriate crimping tool gripping the entire circumference of the crimping channel 100. As the crimping tool is tightened, the notches 101 close as the channel moves together in the direction of the arrows 102. It can be seen that this crimping aspect will replace the set screw 24 disclosed with the previous embodiment for fixing the endplates to the threaded cylindrical body.

While the invention has been illustrated and described in detail in the drawings and foregoing description, the same is to be considered as illustrative and not restrictive in character, it being understood that only the preferred embodiments have been shown and described and that all changes and modifications that come within the spirit of the invention are desired to be protected.

What is claimed is:

1. A vertebral replacement implant for interposition in a space left by one or more removed vertebrae between adjacent intact vertebrae, comprising:

a replacement body having a cylindrical wall defining a hollow interior with opposite ends sized to span a portion of the space between the intact vertebrae, said cylindrical wall defining external threads extending from each of said opposite ends, said wall further defining a plurality of apertures in communication with said hollow interior, said aperture being of substantially equal size; and a pair of endplates each having an end surface for contacting a respective one of the intact vertebrae when the implant is interposed in the space, each of said endplates having a cylindrical portion integrally extending from said end surface, said cylindrical portion defining internal threads configured to threadedly engage said external threads on said replacement body.

2. The vertebral replacement implant according to claim 1, wherein each of said endplates further define a hollow interior.

3. The vertebral replacement implant according to claim 1, wherein the hollow interior of said replacement body is open at said opposite ends.

4. The vertebral replacement implant according to claim 2, further comprising an end cap for closing said bore of one of said endplates at said end surface thereof, said end cap having means for supporting the end cap on the endplate.

5. The vertebral replacement implant according to claim 1, further comprising means for fixing said replacement body to each of said endplates to prevent unthreading of said external and internal threads.

6. The vertebral replacement implant according to claim 5, wherein said means for fixing includes:
   a plurality of openings defined in said cylindrical portion of each of said pair of endplates; and
   a member extendable through one of said plurality of openings into contact with said replacement body.

7. The vertebral replacement implant according to claim 6, wherein:
   said member is a set screw; and
   said number of openings is threaded to receive said set screw in threaded engagement.

8. The vertebral replacement implant according to claim 6, wherein said number of openings are defined in said endplates at said internal threads.

9. The vertebral replacement implant according to claim 1, wherein each of said endplates includes a flange defining said end surface, said flange extending radially outwardly from said cylindrical portion and defining a shape generally corresponding to the shape of a portion of the intact vertebra against which the endplate is in contact.

10. The vertebral replacement implant according to claim 1, wherein said plurality of apertures define an effective area greater than 25% of the surface area of said replacement body.

11. The vertebral replacement implant according to claim 9, wherein said flange defines a number of vascularization apertures therethrough.

12. The vertebral replacement implant according to claim 1, wherein said hollow interior contains bone growth inducing material.

13. A vertebral replacement implant for interposition in a space left by one or more removed vertebrae between adjacent intact vertebrae, comprising:
   a replacement body with opposite ends sized to span a portion of the space between the intact vertebrae, said replacement body including a cylindrical wall defining a hollow interior open at said opposite ends, said cylindrical wall having external threads defined thereon extending from said opposite ends, said replacement body including a central non-threaded portion; and
   a pair of endplates each having an end surface for contacting a respective one of the intact vertebrae when the implant is interposed in the space, each of said endplates having a cylindrical portion integrally extending from said end surface, said endplates each further defining a bore therethrough opening at said end surface and at said cylindrical portion, said bore having internal threads defined thereon at said cylindrical portion configured to threadedly engage the external threads on said replacement body.

14. The vertebral replacement implant according to claim 13, wherein said cylindrical portions include:
   a plurality of threaded openings defined in said cylindrical portion of each of said pair of endplates; and
   a threaded member receivable through said threaded openings to contact said replacement body.

15. The vertebral replacement implant according to claim 14, wherein said replacement body includes a plurality of apertures in communication with said hollow interior.

16. The vertebral replacement implant according to claim 14, wherein each of said endplates includes a flange defining said end surface, said flange extending radially outwardly from said cylindrical portion and defining a shape generally corresponding to the shape of a portion of the intact vertebra against which the endplate is in contact.

17. A vertebral replacement implant for interposition in a space left by one or more removed vertebrae between adjacent intact vertebrae, comprising:
   a replacement body with opposite ends sized to span a portion of the space between the intact vertebrae, said replacement body including a cylindrical wall defining a hollow interior opening at said opposite ends, said cylindrical wall having a thickness of substantially one (1) millimeter, said cylindrical wall having first threads defined thereon; and
   a pair of endplates each having an end surface for contacting a respective one of the intact vertebrae when the implant is interposed in the space, each of said endplates having a cylindrical portion integrally extending from said end surface, said endplates each further defining a bore therethrough opening at said end surface and at said cylindrical portion, said bore having second threads defined thereon at said cylindrical portion configured to threadedly engage the first threads on said replacement body.

18. The vertebral replacement implant according to claim 17, wherein said first threads are external threads and said second threads on said cylindrical portion are internal threads.

19. The vertebral replacement implant according to claim 17, wherein said cylindrical portions include:
   a plurality of threaded openings defined in said cylindrical portion of each of said pair of endplates; and
   a threaded member receivable through said threaded openings to contact said replacement body.

20. The vertebral replacement implant according to claim 19, wherein said replacement body includes a plurality of apertures in communication with said hollow interior.

21. A vertebral replacement implant for interposition in a space left by one or more removed vertebrae between adjacent intact vertebrae, comprising:
   a replacement body including a cylindrical wall defining a hollow interior with opposite ends sized to span a portion of the space between the intact vertebrae, said cylindrical wall defining eternal threads extending from each of said opposite ends, said wall further defining a plurality of apertures in communication with said hollow interior and substantially uniformly distributed about the surface of said cylindrical wall; and
   a pair of endplates each having an end surface for contacting a respective one of the intact vertebrae when the implant is interposed in the space, each of said endplates having a cylindrical portion integrally extending from said end surface, said cylindrical portion having second threads defined thereon configured to threadedly engage the first threads on said replacement body, said endplates including a flange defining said end surface, said flange extending radially outwardly from said cylindrical portion and defining a shape generally corresponding to the shape of a portion of the intact vertebra against which the endplate is in contact.

22. The vertebral replacement implant according to claim 21, wherein said cylindrical portions include:
   a plurality of openings defined in said cylindrical portion of each of said pair of endplates; and
   a threaded member receivable through said threaded openings to contact said replacement body.

23. The vertebral replacement implant according to claim 22, wherein said replacement body includes a plurality of apertures in communication with said hollow interior.

* * * * *